(12) United States Patent
Schon et al.

(10) Patent No.: US 9,763,708 B2
(45) Date of Patent: Sep. 19, 2017

(54) INTRAMEDULLARY FIXATION DEVICE

(71) Applicants: Lew C Schon, Baltimore, MD (US); Jose Antonio Veiga Sanhudo, Porto Alegre RS (BR)

(72) Inventors: Lew C Schon, Baltimore, MD (US); Jose Antonio Veiga Sanhudo, Porto Alegre RS (BR)

(*) Notice: Subject to any disclaimer, the term of this patent is extended or adjusted under 35 U.S.C. 154(b) by 212 days.

(21) Appl. No.: 14/809,512

(22) Filed: Jul. 27, 2015

(65) Prior Publication Data

US 2016/0030094 A1 Feb. 4, 2016

Related U.S. Application Data

(60) Provisional application No. 62/030,234, filed on Jul. 29, 2014.

(51) Int. Cl.
*A61B 17/56* (2006.01)
*A61B 17/58* (2006.01)
*A61F 2/30* (2006.01)
*A61B 17/72* (2006.01)

(52) U.S. Cl.
CPC ...... *A61B 17/7233* (2013.01); *A61B 17/7283* (2013.01)

(58) Field of Classification Search
CPC ..... A61B 17/68; A61B 17/72; A61B 17/7216; A61B 17/7233; A61B 17/7283; A61B 17/7291
USPC .............. 606/60, 62–64, 86 R, 95, 104
See application file for complete search history.

(56) References Cited

U.S. PATENT DOCUMENTS

2009/0270860 A1* 10/2009 Bergin ................ A61F 2/30771
606/62

* cited by examiner

*Primary Examiner* — Ellen C Hammond
*Assistant Examiner* — Christina Negrellirodrigue
(74) *Attorney, Agent, or Firm* — Larry J. Guffey

(57) ABSTRACT

A intramedullary fixation device for use in fixating, after an osteotomy or fracture, segments of a long, tubular bone that has been prepared for the use with the device by cutting into the bone a longitudinal-axis-aligned slot that extends from the free surface to the medullary cavity of the bone, includes: (a) an intramedullary beam whose beam cross-sectional shape varies along the beam's longitudinal axis, (b) a fin whose fin cross-sectional shape varies along the fin's longitudinal axis and a portion of which is attached to the beam surface, (c) wherein the area of any beam cross-sectional section is set so that it can be located in the bone's medullary cavity, and (e) wherein the area of any fin cross section is set so that it can be accommodated in the slot that is cut into the bone.

20 Claims, 4 Drawing Sheets

INTRAMEDULLARY FIXATION DEVICE

CROSS-REFERENCE TO RELATED APPLICATION

This application claims the benefit of Provisional Patent Application No. 62/030,234, filed Jul. 29, 2014 by the present inventors. The teachings of this earlier application are incorporated herein by reference to the extent that they do not conflict with the teaching herein.

BACKGROUND OF THE INVENTION

1. Field of the Invention

The present invention relates generally to surgical devices. More particularly, the invention disclosed herein relates to intramedullary fixation devices.

2. Description of the Related Art

The currently available fixation devices, of which there are many, that are used to treat a long bone fracture or osteotomy are not optimum and therefore need improvement. For example, the currently available fixation devices don't allow stable fixation without an invasive approach that includes opening the adjoining joint and causing irritation of the surrounding soft tissue due to prominence of the profiles of the devices that are attached to the surface of the bones.

Additionally, the prior intramedullary devices provide rotational stability for the treated bones through the use of "locking" screws that are affixed to the bone and require a complex "targeting jig" to correctly align and insert such screws through holes in the intramedullary device. There are also intramedullary devices with deployable elements that are retracted into the intramedullary devices when they are being initially placed into position within the to-be-treated bone or bone segments. These elements diminish the effective thickness of the intramedullary devices in which they are utilized and therefore ultimately weaken the strength of such devices. If the thicknesses or diameters of such devices are increased to accommodate such deployable elements, this can lead to such devices then not being suitable for use in smaller bones whose intramedullary canals are not larger enough to allow for the use of these thicker or larger diameter devices. Finally, such deployable elements have the potential for binding within the intramedullary device and thereby destroying the functionality of such devices.

There are also intramedullary devices that expand or inflate under mechanical pressure in order to affix themselves to the bones that they are being used to treat. These devices require specialized designs, materials of construction and insertion jigs.

Thus, there is a need for the development of improved devices to fixate segments of long bones (e.g., phalanx, metatarsal, metacarpal, radius, ulna, fibula, tibia, femur, humerus, clavicle bone) after an osteotomy or fracture. In certain circumstances, such an improved fixation device might also be used in other types of bones.

SUMMARY OF THE INVENTION

Recognizing the need for the development of an improved device to fixate segments of long bones after an osteotomy or fracture, the present invention is generally directed towards this end.

An improved, intramedullary fixation device for use in fixating, after an osteotomy or fracture, segments of a long, tubular bone, that has a free surface and a medullary cavity, and wherein the bone is prepared for use with the device by cutting into it a longitudinal-axis-aligned slot that extends from the bone's free surface to its medullary cavity, includes: (a) an intramedullary beam having an outer surface, distal and proximate beam ends and a beam length therebetween, a beam longitudinal axis extending between the beam ends, a beam cross-sectional shape whose defining properties, including its area, vary along the beam's longitudinal axis as a function of the distance that any beam cross-section is located from a beam end, (b) a fin having a boundary surface that includes top and bottom portions and distal and proximate fin ends, a fin longitudinal axis extending between the fin ends, a fin cross-sectional shape whose defining properties, including its height and area vary along the fin's longitudinal axis as a function of the distance that any fin cross-section is located from a fin end, (c) wherein the bottom portion of the fin boundary surface is attached to the beam outer surface such that the fin longitudinal axis is parallel to the beam's longitudinal axis, (d) wherein the area of any beam cross-sectional section is set so that the beam can be located in the medullary cavity of the bone whose segments are to be fixated by the device, and (e) wherein the fin is adapted to be accommodated in the slot that is cut into the tubular bone and extends from the tubular bone's free surface to its medullary cavity.

In a variant to this embodiment, the present invention can also take the form of a method for fixating, after an osteotomy or fracture, the segments of such a long, tubular bone, wherein the steps of this method include providing the intramedullary fixation device summarized above, and preparing the bone for the use of the device by cutting a longitudinal-axis-aligned slot into the bone that extends from the free surface to the medullary cavity of the bone.

Thus, there has been summarized above (rather broadly and understanding that there are other aspects which have not been summarized above) the present invention in order that the detailed description that follows may be better understood and appreciated.

DESCRIPTION OF THE PREFERRED EMBODIMENT

Figure 1:
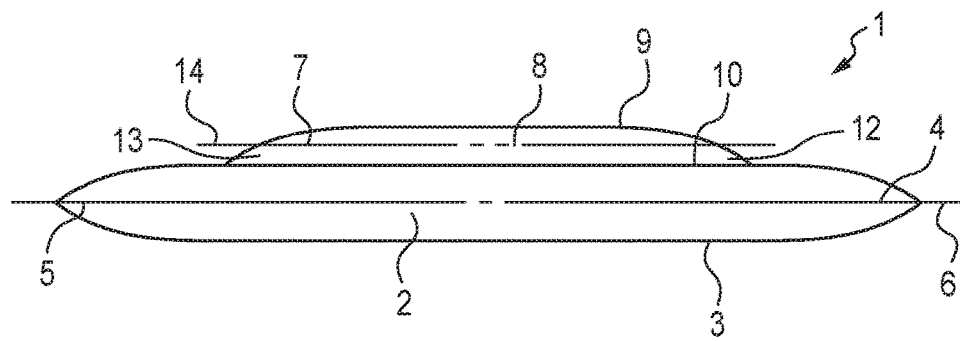
FIG. 1 is a lateral view of a preferred embodiment of the present invention.
Figure 2:
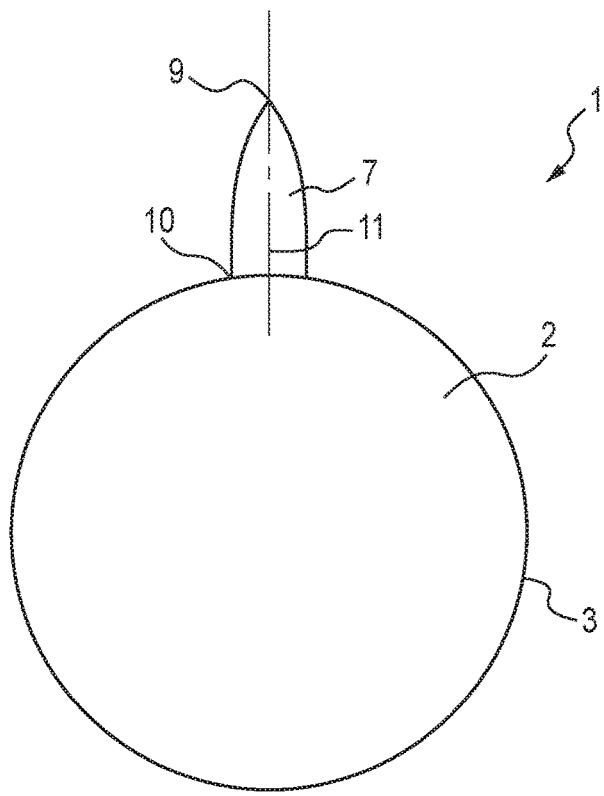
FIG. 2 is an enlarged, end view of the embodiment shown in FIG. 1.
Figure 3:
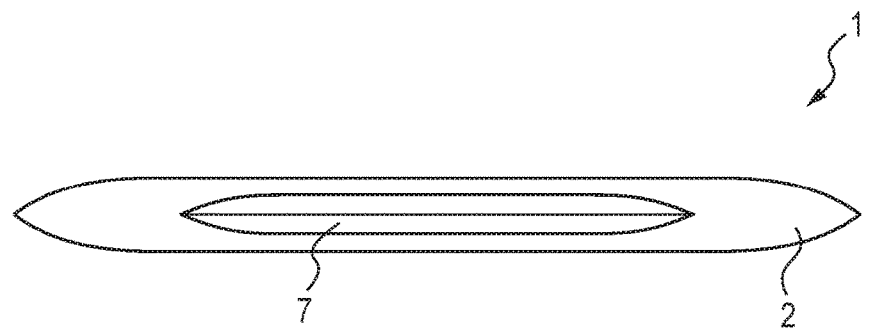
FIG. 3 is a superior view of the embodiment shown in FIG. 1.
Figure 4:
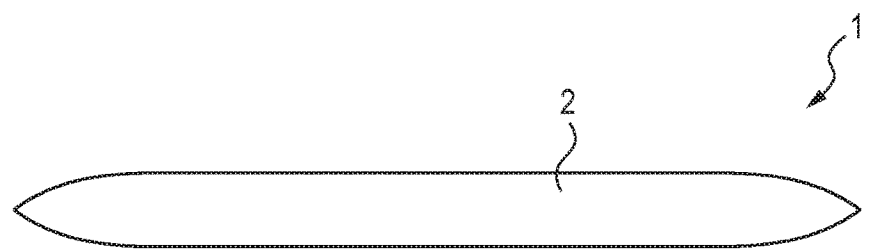
FIG. 4 is an inferior view of the embodiment shown in FIG. 1.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention is a device or implant 1, which may be called a "finned beam," is a fixation device that provides osteotomy-fragment-fracture stabilization without opening the adjacent joint or causing soft tissue irritation. In addition, it allows either shortening, lengthening, straitening or rotational correction of the osteotomy or fracture. This permits stability of the fracture or osteotomy and promotes healing of the bone in the corrected position.

An intramedullary beam 2 makes up the bulk of the implant and is configured for introduction into the medullary or metatarsal canal of a long bone after a slice of the bone's neck has been removed. Such an intramedullary beam has an outer surface 3, distal 4 and proximal 5 beam ends and a beam length therebetween, a beam longitudinal axis 6 extending between the beam ends, a beam cross-sectional shape that is perpendicular to the beam longitudinal axis and whose defining properties, including its area, vary along the beam's longitudinal axis as a function of the distance that any beam cross-section is located from one of the beam's ends. Additionally, the area of any beam cross-sectional section is set so that the beam can be located in the medullary cavity of a tubular bone whose segments are to be fixated by the device.

See FIGS. 1-4.

A longitudinally-aligned fin 7 protrudes from the beam. This fin has a boundary surface 8 that includes top 9 and bottom 10 portions and a vertical axis 11 that extends therebetween, distal 12 and proximal 13 fin ends and a fin length therebetween, a fin longitudinal axis 14 extending between the fin ends, a fin cross-sectional shape that is perpendicular to the fin longitudinal axis and whose defining properties, including its height between its top and bottom portions of any cross-section and its area, vary along the fin's longitudinal axis as a function of the distance that any fin cross-section is located from the fin's ends.

The bottom 10 portion of the fin boundary surface is attached to the beam outer surface 3 such that the fin longitudinal axis is parallel to the beam's longitudinal axis and the fin's vertical axis is perpendicular to the beam's longitudinal axis. Additionally, the fin is adapted to be accommodated in the tubular bone by sizing the fin such that it is accommodated, when the beam is situated in the medullary cavity of the tubular bone, into a slot that is cut into the tubular bone and extends from the tubular bone's free surface to its medullary cavity. The fin height is then chosen so that the top portion of the fin, when the fin is situated in the slot, does not extend beyond the free surface of the tubular bone.

The present invention is fabricated as a solid one-piece construct in order to maximize its strength. Its fin 7 provides intrinsic bone stability without a complex targeting jig, deployment mechanisms or mechanical alterations. Its utilization need not affect the adjacent joint. Meanwhile, the beam's cross-sectional shape is generally round (although it could also assume other shapes, e.g., oval, polygonal) and its characterizing diameter varies along its length to fit the medullary canal into which it is to be situated (i.e., the area of any beam cross section is adapted so that it is locatable in the medullary cavity of the bone). Its proximal and the distal ends are tapered so that they take on a shape that can be described as providing the beam with spiked ends.

The fin 7 of the present invention is generally fabricated for the specific bone that it is to be used to treat. The height of this fin is adjusted so that it is less than or equal to the thickness of the cortex of the bone which it is being used to treat. This fin is optimally shorter than the length of the beam, but, in certain circumstances, it may be equal or longer.

The preferred material of construction for this implant is a biocompatible material or combination of materials, e.g., bone (xenograft or allograft), calcium phosphate, hydroxyapatite, plastic, metallic (titanium or stainless steel), ceramic. Its fabrication methods may involve molding, milling or extrusion. The implant may be coated for additional fixation or medical drug or biologic delivery (e.g., growth factor, antibiotic, stem cells, ingrowth materials). It may also have additional surface features (e.g., holes, recesses, porous coatings or troughs) to optimize bone stability, healing or insertion techniques.

The present invention provides a stable osteotomy fixation without causing surrounding soft tissue irritation and eliminates intervention into the adjacent joints. After implantation, the two fragments of bone are intramedullary fixated with no soft tissue implant irritation.

Use of the present invention may include the following procedures: after the skin incision, the long bone is approached and with a microsaw, an osteotomy is performed longitudinally at the dorsal cortex, as a slot; at the middle of this longitudinal osteotomy, a transverse cut is initiated, but not completed. Another perpendicular and distal cut is performed by reaching the inferior cortex, at a pre-established distance, depending on the amount of desired shortening, to restore an adequate length. The saw is then proximally turned to the osteotomy sulcus until its completion; the resulting slice is then removed.

Figure 5A:
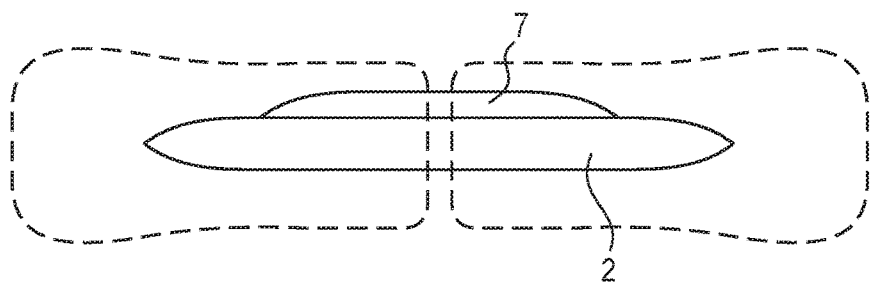
FIG. 5(a) is a lateral view of a preferred embodiment of the present invention being use in a metatarsal bone whose outline is shown in dashed lines.
Figure 5B:
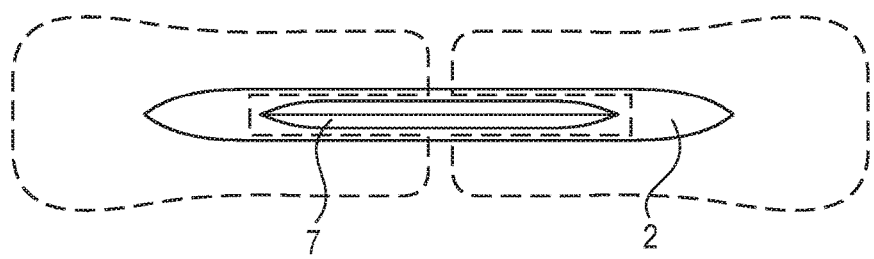
FIG. 5(b) is a superior view of the preferred embodiment being used in a metatarsal bone as shown in FIG. 5(a).

The device of the present invention is partially introduced into the proximal intramedullary canal with its fin 7 upwardly directed, penetrating the bone's slot (longitudinal osteotomy), and leaving one of the beam's pointed or spiked ends proximally pushed toward the shaft axis, thus promoting an intramedullary osteotomy fixation. See FIGS. 5(a)-5(b) that show a version of the present invention being used in a metatarsal bone.

Advantages of the present invention include: (a) Strength: once it's a solid implant, its strength is high, (b) Three point or stable intramedullary fixation, (c) Simple manufacturing, sterilization, packaging—may mean lower implant cost, (d) Ease of insertion, (e) No need for special targeting jigs that often use radiation (x-ray) for screw alignment, (f) Versatility, as it can be used in many bones, (g) Biologic enhancement may be possible depending on surface modifications, and (h) Infection treatment is possible bases on materials and surface modifications.

The foregoing is considered as illustrative only of the principles of the present invention. Further, since numerous modifications and changes will readily occur to those skilled in the art, it is not desired to limit the invention to the exact construction and operation shown and described herein.

Figure 6A:
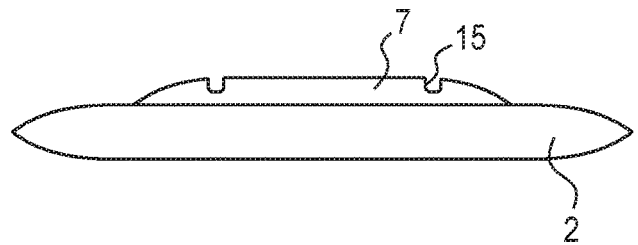
FIG. 6(a) shows a side view of a different version of the present invention that is intended to address the problem of potential gapping between the two parts of a long bone that result after it has been completely, laterally cut at some point along its longitudinal axis.
Figure 6B:
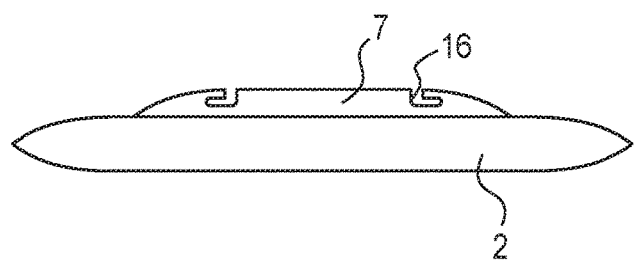
FIG. 6(b) shows a side view of another variation of the embodiment shown in FIG. 6(a).
Figure 6C:
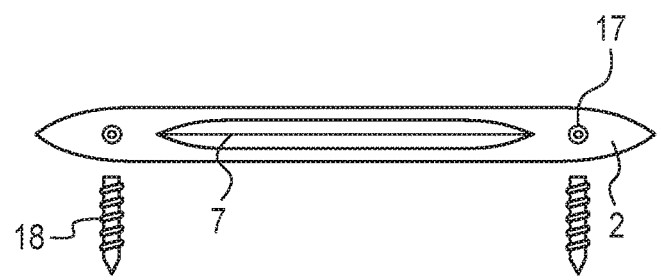
FIG. 6(c) shows a side view of yet another variation of the embodiment shown in FIG. 6(a).

For example, it may be necessary to modify the outer surface 3 of the beam 2 in order to address different, foreseeable problems with the use of the present invention. FIGS. 6(a)-6(c) show different versions of the present invention that are intended to address the problem of potential gapping between the two parts of a long bone that result after it has been completely, laterally cut at some point along its longitudinal axis.

FIG. 6(a) shows a side view of a fin 7 having notches 15 in the top portion of its boundary surface 8. Placement of a small hole in the top portion and near the uncut end of one of the pieces of the long bone being treated allows the end of one of the tines or prongs of a clamp to be fitted into this hole while the other tine end is placed is this notch 15 and then pressure is exerted of the outside edges of the clamp's prongs so as to force them closer together and by doing so causes the beam's end to be forced deeper into the intramedullary canal of this piece of the bone being treated. Alternatively, using two prongs, one of which works on each notch and a hole in the nearest end the two pieces of the bone being treated, allows the pieces of bone to be brought closer together until their cut edges actually touch and have compressive forces applied to them.

FIG. 6(b) shows a side view of a fin 7 having holes or notches with undercut reliefs 16 in the top portion of its boundary surface 8. Placement of a small hole, in the top portion on either side of the slot that was cut into the bone to accommodate the beam's fin and near the uncut end of one of the pieces of the long bone being treated, allows a suture to be attached at these small holes and then looped around the fin's undercut reliefs and used to apply a tension force on the fin so as to cause the beam's end to be forced deeper into the intramedullary canal of the piece of the bone being treated in this manner. Doing this same type of hole drilling and suture typing in both of the pieces of a being treated bone allows the two bone pieces to be drawn together so that their cut edges actually touch and have compressive forces applied to them.

FIG. 6(c) shows a beam 2 having threaded screw recesses 17 that have been drilled into the top portion of the beam's outer surface 3 on either end of it's fin. A hole that extends from the top portion of a being treated bone and into its intramedullary canal is used to allow a threaded screw 18 to be passes through such a hole and be screwed into the recess in order to further secure the implant 1 to the bone.

It is noted that one or more of the above-discussed features of the present invention may be independently incorporated into some embodiments without necessarily incorporating other features. It is also contemplated that numerous additions and modifications can be made to the present invention.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention.

We claim:

1. An intramedullary fixation device for use, after an osteotomy or fracture, in fixating segments of a long, tubular bone that has ends, a free surface and a medullary cavity and a longitudinal axis which extends between said ends, and wherein said bone is prepared for use with said intramedullary fixation device by cutting a longitudinal-axis-aligned slot into said bone that extends from the free surface to the medullary cavity of said bone, said device comprising:
an intramedullary beam having an outer surface and distal and proximate beam ends, and wherein the geometry of said outer surface of said intramedullary beam varies along a longitudinal axis that extends between said beam ends, and wherein said outer surface geometry is quantifiable in terms of the area of a beam cross section that is taken perpendicular to said beam longitudinal axis and wherein said area varies as a function of the distance that said cross section is located from a beam end,
a fin having a boundary surface that includes top and bottom portions, and distal and proximate beam ends, and wherein the geometry of said boundary surface of said fin varies along a fin longitudinal axis that extends between said fin ends, and wherein said boundary surface geometry is quantifiable in terms of the area and height, between said top and bottom portions, of a fin cross section that is taken perpendicular to said fin longitudinal axis and wherein said fin area and height vary as a function of the distance that said cross section is located from a fin end,
wherein said bottom portion of said fin boundary surface is attached to said beam outer surface such that said fin longitudinal axis is parallel to said beam longitudinal axis,
wherein said area of any said beam cross section is adapted so that said beam is locatable in the medullary cavity of a specific long, tubular bone whose segments are to be fixated by said device, and
wherein said area of any said fin cross section is adapted so that said fin is locatable, when said beam is situated in the medullary cavity of said specific long, tubular bone, in said longitudinal-axis-aligned slot that has been cut into said specific long, tubular bone.

2. The intramedullary fixation device as recited in claim 1, wherein:
said fin height is chosen so that the top portion of said fin, when said fin is situated in said longitudinal-axis-aligned slot, does not extend beyond the free surface of said specific long, tubular bone.

3. The intramedullary fixation device as recited in claim 1, wherein:
the area of said beam cross sections diminishes as the beam longitudinal axis is traversed in moving towards an end of said beam so as to provide said end with a tapered shape.

4. The intramedullary fixation device as recited in claim 2, wherein:
the area of said beam cross sections diminishes as the beam longitudinal axis is traversed in moving towards an end of said beam so as to provide said end with a tapered shape.

5. The intramedullary fixation device as recited in claim 1, wherein:
said top portion of said fin having a notch with a configuration adapted to aid in positioning said device in the medullary cavity of a specific long, tubular bone whose segments are to be fixated by said device.

6. The intramedullary fixation device as recited in claim 2, wherein:
said top portion of said fin having a notch with a configuration adapted to aid in positioning said device in the medullary cavity of a specific long, tubular bone whose segments are to be fixated by said device.

7. The intramedullary fixation device as recited in claim 3, wherein:
said top portion of said fin having a notch with a configuration adapted to aid in positioning said device in the medullary cavity of a specific long, tubular bone whose segments are to be fixated by said device.

8. The intramedullary fixation device as recited in claim 4, wherein:
said top portion of said fin having a notch with a configuration adapted to aid in positioning said device in the medullary cavity of a specific long, tubular bone whose segments are to be fixated by said device.

9. The intramedullary fixation device as recited in claim 7, wherein:
said outer surface of said intramedullary beam having a recess with a configuration adapted to aid in securing said device to a specific long, tubular bone whose segments are to be fixated by said device.

10. The intramedullary fixation device as recited in claim 8, wherein:
said outer surface of said intramedullary beam having a recess with a configuration adapted to aid in securing said device to a specific long, tubular bone whose segments are to be fixated by said device.

11. A method for fixating, after an osteotomy or fracture, the segments of a long, tubular bone that has ends, a free surface and a medullary cavity and a longitudinal axis which extends between said ends, said method comprising the steps of:
providing an intramedullary fixation device,
preparing said bone for the use of said intramedullary fixation device by cutting a longitudinal-axis-aligned slot into said bone that extends from the free surface to the medullary cavity of said bone,
wherein said intramedullary fixation device comprising:
an intramedullary beam having an outer surface and distal and proximate beam ends, and wherein the geometry of said outer surface of said intramedullary beam varies along a longitudinal axis that extends between said beam ends, and wherein said outer surface geometry is quantifiable in terms of the area of a beam cross section that is taken perpendicular to said beam longitudinal axis and wherein said area varies as a function of the distance that said cross section is located from one of said beam ends, and with the distance between said distal and proximate beam ends defining the length of said beam,
a fin having a boundary surface that includes top and bottom portions, and distal and proximate beam ends, and wherein the geometry of said boundary surface of said fin varies along a fin longitudinal axis that extends between said fin ends, and wherein said boundary surface geometry is quantifiable in terms of the area and height, between said top and bottom portions, of a fin cross section that is taken perpendicular to said fin longitudinal axis and wherein said area and height vary as a function of the distance that said cross section is located from one of said fin ends, and with the distance between said distal and proximate fin ends defining the length of said fin,
wherein said bottom portion of said fin boundary surface is attached to said beam outer surface such that said fin longitudinal axis is parallel to said beam longitudinal axis and said fin vertical axis is perpendicular to said beam longitudinal axis,
wherein said area of any said beam cross section is adapted so that said beam is locatable in the medullary cavity of a specific long, tubular bone whose segments are to be fixated by said device, and
wherein said area of any said fin cross section is adapted so that said fin is locatable, when said beam is situated in the medullary cavity of said specific long, tubular bone, in said longitudinal-axis-aligned slot that has been cut into said specific long, tubular bone.

12. The method as recited in claim 11, wherein:
said fin height is chosen so that the top portion of said fin, when said fin is situated in said longitudinal-axis-aligned slot, does not extend beyond the free surface of said specific long, tubular bone.

13. The method as recited in claim 11, wherein:
the area of said beam cross sections diminishes as the beam longitudinal axis is traversed in moving towards an end of said beam so as to provide said end with a tapered shape.

14. The method as recited in claim 12, wherein:
the area of said beam cross sections diminishes as the beam longitudinal axis is traversed in moving towards an end of said beam so as to provide said end with a tapered shape.

15. The method as recited in claim 11, wherein:
said top portion of said fin having a notch with a configuration adapted to aid in positioning said device in the medullary cavity of a specific long, tubular bone whose segments are to be fixated by said device.

16. The method as recited in claim 12, wherein:
said top portion of said fin having a notch with a configuration adapted to aid in positioning said device in the medullary cavity of a specific long, tubular bone whose segments are to be fixated by said device.

17. The method as recited in claim 13, wherein:
said top portion of said fin having a notch with a configuration adapted to aid in positioning said device in the medullary cavity of a specific long, tubular bone whose segments are to be fixated by said device.

18. The method as recited in claim 14, wherein:
said top portion of said fin having a notch with a configuration adapted to aid in positioning said device in the medullary cavity of a specific long, tubular bone whose segments are to be fixated by said device.

19. The method as recited in claim 17, wherein:
said outer surface of said intramedullary beam having a recess with a configuration adapted to aid in securing said device to a specific long, tubular bone whose segments are to be fixated by said device.

20. The method as recited in claim 18, wherein:
said outer surface of said intramedullary beam having a recess with a configuration adapted to aid in securing said device to a specific long, tubular bone whose segments are to be fixated by said device.

* * * * *